United States Patent
Lorenzo et al.

(10) Patent No.: US 11,589,874 B2
(45) Date of Patent: Feb. 28, 2023

(54) SPLIT BALLOON ASSIST DEVICE AND METHOD FOR USING THE SAME

(71) Applicant: DePuy Synthes Products, Inc., Raynham, MA (US)

(72) Inventors: Juan Lorenzo, Raynham, MA (US); Robert Slazas, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 320 days.

(21) Appl. No.: 17/022,909

(22) Filed: Sep. 16, 2020

(65) Prior Publication Data

US 2020/0405319 A1    Dec. 31, 2020

Related U.S. Application Data (62) Division of application No. 15/941,105, filed on Mar. 30, 2018, now Pat. No. 10,786,259.

(51) Int. Cl.
*A61B 17/12* (2006.01)
*A61M 25/10* (2013.01)
(Continued)

(52) U.S. Cl.
CPC .... *A61B 17/12136* (2013.01); *A61B 17/1204* (2013.01); *A61B 17/12109* (2013.01); *A61M 25/10* (2013.01); *A61M 25/1002* (2013.01); *A61M 25/1011* (2013.01); *A61M 25/10181* (2013.11); *A61B 17/0218* (2013.01);
(Continued)

(58) Field of Classification Search
CPC ............ A61B 17/0218; A61B 17/1204; A61B 17/12109; A61B 17/12136; A61B 2017/00296; A61B 2017/00557; A61B 2017/1205; A61B 2017/22067; A61M 25/10; A61M 25/1002; A61M 25/1011; A61M 25/1018; A61M 25/10181; A61M 25/1025; A61M 25/1034; A61M 2025/1043; A61M 2025/1052; A61M 2025/1072; A61M 2205/0216
See application file for complete search history.

(56) References Cited

U.S. PATENT DOCUMENTS

| 3,811,448 A | 5/1974 | Morton |
| 4,762,130 A | 8/1988 | Fogarty |

(Continued)

FOREIGN PATENT DOCUMENTS

| CN | 105682610 A | 6/2016 |
| EP | 0 275 230 A2 | 7/1988 |

(Continued)

OTHER PUBLICATIONS

Extended European Search Report from corresponding European application No. 19166296.4, dated Aug. 29, 2019.

*Primary Examiner* — Jocelin C Tanner
(74) *Attorney, Agent, or Firm* — Troutman Pepper Hamilton Sanders LLP (57) ABSTRACT

A method is disclosed, including joining a balloon to a resilient inner body of a balloon assist device, the balloon comprising an axial length shorter than an axial length of the inner body; expanding a slit in the resilient inner body of the balloon assist device; inserting a catheter through the slit; and releasing the slit to contract the balloon assist device around the catheter.

11 Claims, 7 Drawing Sheets

(51) Int. Cl.
    *A61B 17/00* (2006.01)
    *A61B 17/02* (2006.01)
(52) U.S. Cl.
    CPC .............. *A61B 2017/00557* (2013.01); *A61M 2025/1043* (2013.01); *A61M 2025/1052* (2013.01); *A61M 2025/1072* (2013.01); *A61M 2205/0216* (2013.01)

(56) References Cited

U.S. PATENT DOCUMENTS

| | | | |
|---|---|---|---|
| 5,181,911 A | 1/1993 | Shturman | |
| 5,211,654 A | 5/1993 | Kaltenbach | |
| 5,226,888 A | 7/1993 | Arney | |
| 5,295,958 A | 3/1994 | Shturman | |
| 5,549,555 A | 8/1996 | Sohn | |
| 5,554,119 A | 9/1996 | Harrison et al. | |
| 5,772,681 A | 6/1998 | Leoni | |
| 5,797,948 A | 8/1998 | Dunham | |
| 5,843,027 A | 12/1998 | Stone et al. | |
| 5,855,546 A | 1/1999 | Hastings et al. | |
| 5,882,334 A * | 3/1999 | Sepetka | A61M 25/104 604/164.08 |
| 5,919,163 A | 7/1999 | Glickman | |
| 6,196,996 B1 | 3/2001 | Teirstein | |
| 6,391,037 B1 | 5/2002 | Greenhalgh | |
| 6,398,708 B1 | 6/2002 | Hastings et al. | |
| 6,409,652 B1 | 6/2002 | Kamdar et al. | |
| 6,544,276 B1 | 4/2003 | Azizi | |
| 6,575,932 B1 | 6/2003 | O'Brien et al. | |
| 6,666,828 B2 | 12/2003 | Greco et al. | |
| 7,081,115 B2 | 7/2006 | Taimisto | |
| 7,214,198 B2 | 5/2007 | Greco et al. | |
| 7,300,415 B2 | 11/2007 | McMurtry et al. | |
| 7,766,871 B2 | 8/2010 | Hirszowicz | |
| 8,079,978 B2 | 12/2011 | Hirszowicz et al. | |
| 9,149,288 B2 | 10/2015 | Teague et al. | |
| 9,180,033 B2 | 11/2015 | Motaganahalli | |
| 9,232,992 B2 | 1/2016 | Heidner | |
| 9,345,864 B2 | 5/2016 | Suehara | |
| 9,398,965 B2 | 7/2016 | Motaganahalli | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 10,219,678 B2 | 3/2019 | Wake | |
| 10,286,184 B2 | 5/2019 | Laduca | |
| 2002/0045925 A1 | 4/2002 | Keller et al. | |
| 2004/0176790 A1* | 9/2004 | Coyle | A61M 25/104 606/194 |
| 2005/0197667 A1 | 9/2005 | Chan et al. | |
| 2006/0030924 A1 | 2/2006 | Van Der Leest et al. | |
| 2006/0064151 A1 | 3/2006 | Guterman | |
| 2006/0074437 A1 | 4/2006 | Teague et al. | |
| 2006/0287666 A1 | 12/2006 | Saadat et al. | |
| 2007/0185444 A1* | 8/2007 | Euteneuer | A61M 25/1027 604/96.01 |
| 2008/0281350 A1 | 11/2008 | Sepetka | |
| 2009/0209969 A1 | 8/2009 | Wolfe | |
| 2010/0145265 A1 | 6/2010 | Min et al. | |
| 2010/0324649 A1 | 12/2010 | Mattsson | |
| 2011/0137331 A1 | 6/2011 | Walsh et al. | |
| 2011/0144742 A1 | 6/2011 | Madrid et al. | |
| 2012/0226303 A1 | 9/2012 | Roche et al. | |
| 2012/0245520 A1 | 9/2012 | Kelly et al. | |
| 2012/0283768 A1 | 11/2012 | Cox et al. | |
| 2014/0135812 A1 | 5/2014 | Divino et al. | |
| 2014/0135891 A1 | 5/2014 | Pohelmann et al. | |
| 2014/0200607 A1 | 7/2014 | Sepetka et al. | |
| 2014/0249506 A1 | 9/2014 | Laduca | |
| 2014/0343409 A1 | 11/2014 | Purtell et al. | |
| 2015/0238729 A1 | 8/2015 | Jenson et al. | |
| 2015/0320982 A1 | 11/2015 | Massicotte | |
| 2016/0310759 A1 | 10/2016 | D'Andrea | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042645 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo | |
| 2017/0106173 A1 | 4/2017 | Chanduszko | |
| 2017/0113023 A1 | 4/2017 | Steingisser et al. | |
| 2017/0147765 A1 | 5/2017 | Mehta | |

(56) References Cited

U.S. PATENT DOCUMENTS

| | | |
|---|---|---|
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0014829 A1 | 1/2018 | Tal et al. |

FOREIGN PATENT DOCUMENTS

| | | |
|---|---|---|
| EP | 2589344 A1 | 5/2013 |
| JP | 2013-223663 A | 10/2013 |
| WO | 99/27989 A1 | 6/1999 |
| WO | 2015/061801 A2 | 4/2015 |
| WO | WO 2017/081561 A1 | 5/2017 |

* cited by examiner

SPLIT BALLOON ASSIST DEVICE AND METHOD FOR USING THE SAME

CROSS REFERENCE TO RELATED APPLICATION

The present application is a divisional application of U.S. patent application Ser. No. 15/941,105 filed Mar. 30, 2018. The entire contents of which are hereby incorporated by reference.

FIELD

This disclosure relates generally to the field of tools for vascular surgery. More particularly, it relates to balloon devices for occluding blood vessels during vascular surgery.

BACKGROUND

Balloon Guide Catheters facilitate the insertion of intravascular devices as well as control/restrict flow in ischemic applications. They are designed to have a large lumen to maximize clot capture, and are indicated for use as a conduit for clot retrieval devices. Because the balloon is an integral part of the assembly on these devices, the profile of the devices is very large, for example 8F (2.7 mm) (French "F"=0.33 mm) as compared to a regular large ID guide catheter which might be sized 6 F (2.0 mm). Also, the overall flexibility of the system is decreased due to the required inflation lumen and dual layer construction needed to inflate the distal balloon. The combination of the large overall profile and the lack of distal flexibility makes tracking these devices in the neurovascular anatomy difficult. Accordingly, use of these devices is mostly limited to the proximal cerebral vasculature.

SUMMARY

To address these deficiencies in the existing art, a balloon assist device is disclosed which includes an inner body and a sheath joined to the inner body, enclosing a volume between the inner body and the sheath. The inner body extends along an axis from a proximal end to a distal end and the cross-section of the inner body partially encloses the axis. The balloon assist device also includes an inflation tube in sealed communication with the volume enclosed by the inner body and the sheath. The balloon assist device may also include a pusher for sliding the balloon assist device along the catheter. The pusher may extend parallel to the axis from the proximal end of the balloon assist device in a proximal direction. The inflation tube may also be used as a pusher. The inner body of the balloon assist device may be a split cylinder extending along the axis from the proximal end to the distal end. The inner body may be formed of a resilient material.

The split cylinder of the inner body is divided by a slit. The slit may be straight, parallel to the axis from the proximal end to the distal end or helical, extending helically about the axis from the proximal end to the distal end. The sheath may be bonded to inner body along a perimeter having four sides which follow the contours of an outer face of the split cylinder. The sheath may be an elastic material or an inelastic material.

The balloon assist device may be designed for the inner body to snap over the exterior of a catheter with the inflatable sheath bonded to the inner body, for example by passing the catheter through a slit in the inner body. The inner body may be slidable along the catheter when snapped over the exterior of the catheter. The balloon assist device may be slid along the catheter via the pusher extending from the balloon assist device in a proximal direction. The balloon assist device may include an inflation tube in sealed communication with the inflatable sheath. The inflation tube may also be used to slide the balloon assist device along the catheter. The inner body may be formed of a resilient material configured to snap over the exterior of the catheter by expanding a slit in the inner body, passing the catheter through the slit, and allowing the slit to contract around the catheter.

A balloon assisted catheter system includes a catheter and a balloon assist device including an inner body and an inflatable sheath bonded to the inner body. The inner body may include a split cylinder with a proximal and a distal end. The split cylinder may be split by a straight opening extending from the proximal end to the distal end or by a helical opening extending helically about the axis from the proximal end to the distal end. The balloon assist device may include a pusher extending from the balloon assist device in a proximal direction. The pusher may be used to slide the balloon assist device along the catheter. The balloon assist device may also include an inflation tube in sealed communication with the inflatable sheath.

A method of using a balloon assist device including the steps of expanding a slit in a resilient inner body of the balloon assist device, inserting a catheter through the expanded slit, and releasing the expanded slit to contract around the catheter. The method may also include using a pusher to slide the balloon assist device along the catheter to a treatment site in a patient's vasculature. The method may also include using an inflation tube to inflate the balloon assist device at the treatment site. The method may also include performing a surgical procedure while the inflated balloon assist device occludes a blood vessel at the treatment site. The method may also include deflating the balloon assist device and withdrawing the deflated balloon assist device.

DETAILED DESCRIPTION

Figure 1:
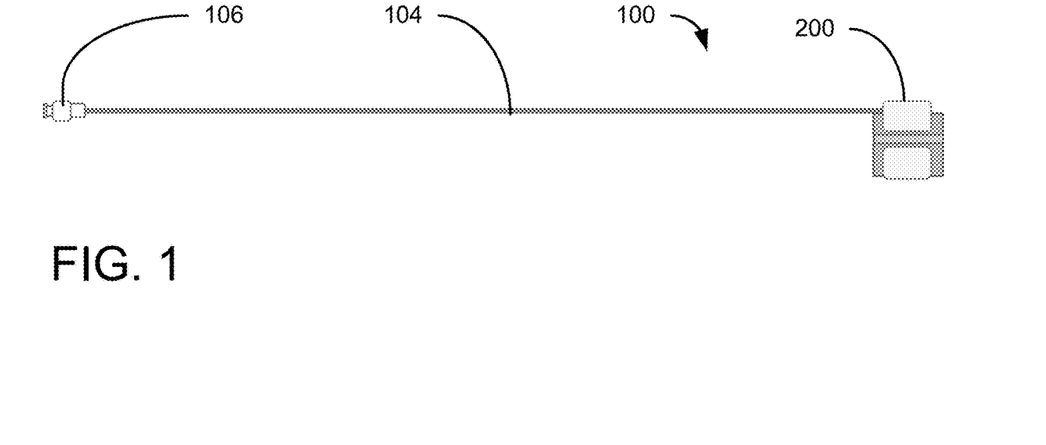
FIG. 1 is a diagram of a balloon assist device illustrating is basic components, in accordance with the present disclosure.
Figure 2:
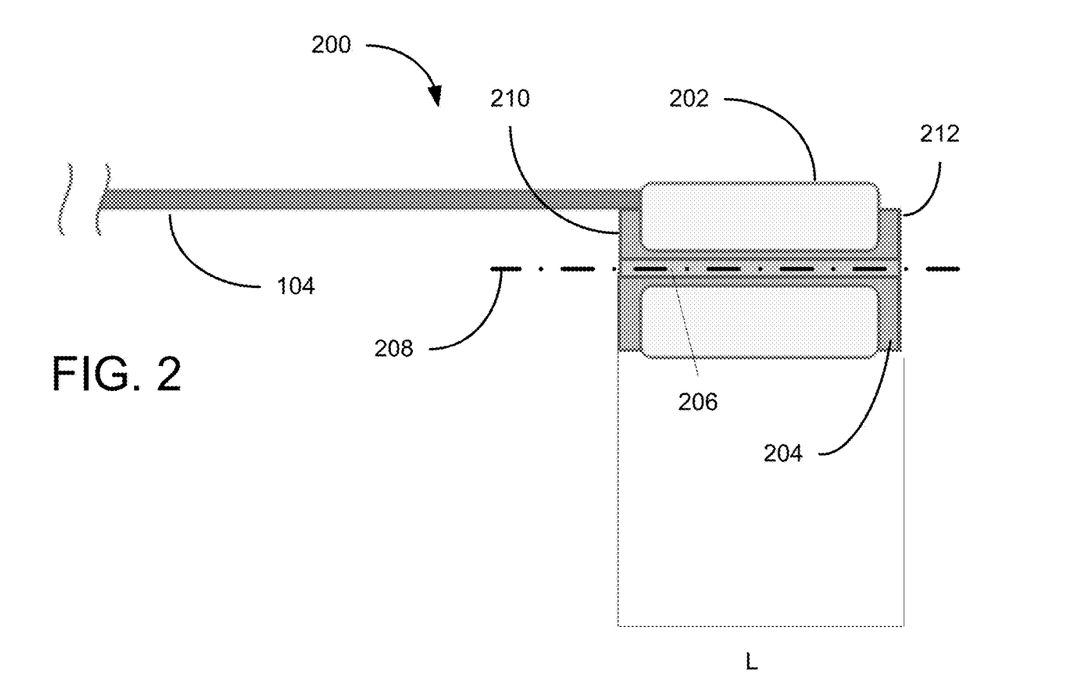
FIG. 2 is a diagram of the balloon assembly of the balloon assist device illustrating is construction, in accordance with the present disclosure.
Figure 3:
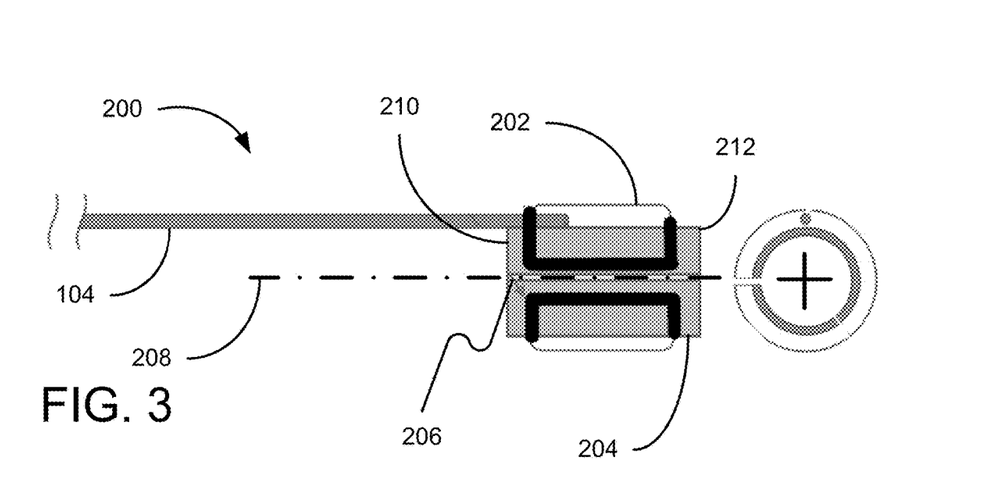
FIG. 3 is a diagram of the balloon assembly of the balloon assist device illustrating the balloon in the deflated state and highlighting the seals between the balloon and the inner body, in accordance with the present disclosure.
Figure 4:
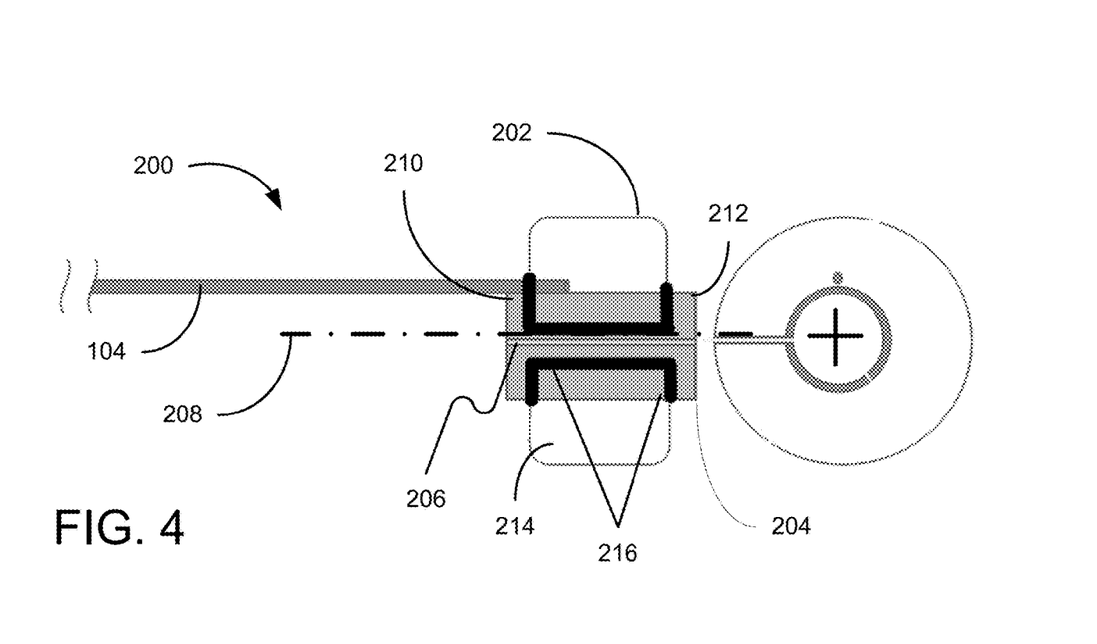
FIG. 4 is a diagram of the balloon assembly of the balloon assist device illustrating the balloon in the inflated state and highlighting the seals between the balloon and the inner body, in accordance with the present disclosure.

Referring now to the Figures, in which like reference numerals represent like parts, various embodiments of the balloon assist device and methods of using it will be disclosed in detail. FIG. 1 is a diagram of the balloon assist device 100 illustrating is basic components. The balloon assist device 100 includes a balloon assembly 200, an inflation tube 104, and an inflation port 106. FIG. 2 is a closer view of the balloon assembly 200. The balloon assembly 200 includes the balloon 202 fixed to an inner body 204. In an alternate example, the inner body 204 can be formed integrally to the balloon 202. The inner body extends along an axis 208 from a proximal end 210 to a distal end 212 and includes a slit 206 used to mount the balloon assist device 100 to a catheter. Thus, the inner body 204 partially encloses the axis 208. FIGS. 3 and 4 illustrate one embodiment of attaching the balloon 202 to the inner body 204. In this embodiment, the balloon 202 includes a sheath 214 of flexible material which is joined to the inner body 204 around the perimeter 216 of the sheath 214. The sheath 214 may be made of an appropriate elastic or inelastic material, including polyimide. The volume enclosed between the sheath 214 and inner body 204 becomes the balloon 202.

FIG. 3 illustrates the balloon 202 in the deflated state. FIG. 4 illustrates the balloon 202 in the inflated state. Although a particular shape of the balloon 202 is illustrated, the disclosure is not limited to the shape shown. The balloon 202 is inflated using the inflation tube 104. Sterile water, saline or another appropriate solution may be introduced to the inflation tube 104 at the inflation port 106. The inflation port 106 may be one of several types known in the industry. In another embodiment, the balloon 202 and the inner body 204 are formed integrally with one another.

The slit 206 is provided along a length L of, and in certain examples, entirely through the length of the inner body 204 to permit the balloon assist device to mount to the exterior of a catheter 240. The catheter 240 can be as small as 6-8 F, which enhances ability of the invention to access distal vasculature. To mount the balloon assist device 100 on the catheter 240, the slit 206 is spread open and the catheter 240 is passed through the slit. The slit 206 is then reclosed. In one embodiment, the inner body 204 is made of a resilient material such as spring-temper stainless steel or, more preferably a superelastic material such as Nitinol. In such an embodiment, the slit 206 in the inner body 204 will reclose on its own due to the resilient nature of the inner body 204. In another embodiment the inner body 204 is formed integrally with the balloon 202.

Figure 5:
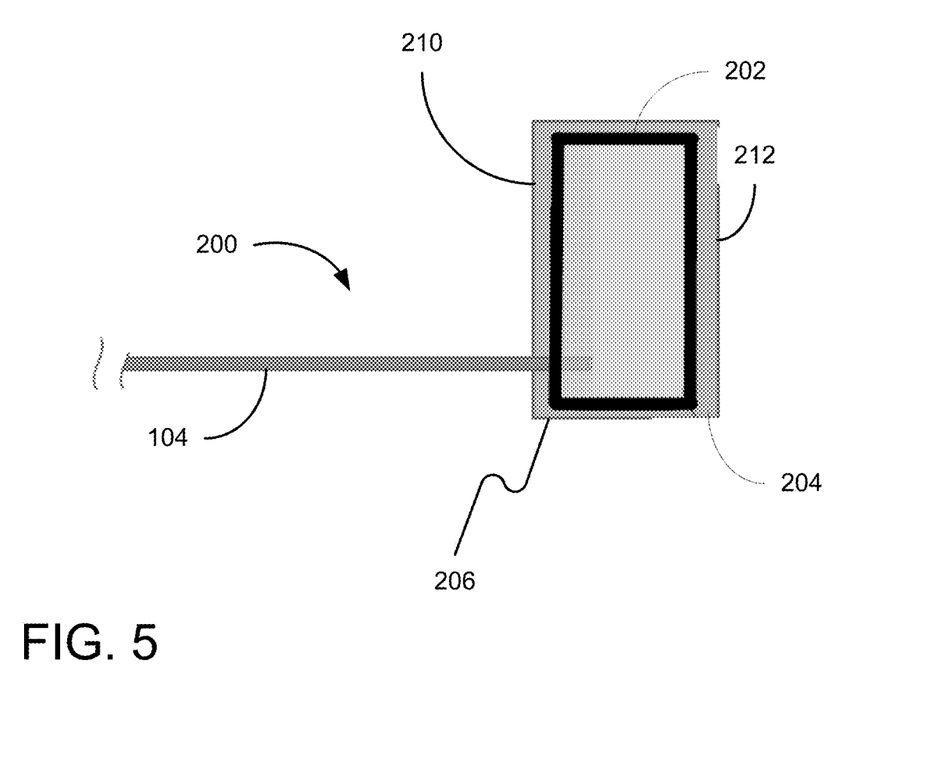
FIG. 5 is a diagram of the balloon assembly of the balloon assist device illustrating the balloon and inner body in a flattened state, in accordance with the present disclosure.

FIG. 5 illustrates one example where the balloon assembly 200 is first assembled in a flat configuration, where the shape of the inner body 204 and the sheath 214 can be more easily cut. The flat configuration also allows easier sealing of the sheath 214 to the inner body 204 around the sheath's perimeter 216. The sheath 214 may be sealed to the inner body 204 using a variety of techniques well-known in the industry including, without limitation, adhesives, thermal bonding, and radio-frequency (RF) bonding. In addition to the seal between the sheath 214 and in the inner body 204, the inflation tube 104 is in sealed communication with the inner volume of the balloon 202. The inflation tube 104 may be made from metal to facilitate pushability of the balloon 202 along the catheter 240, a polymeric material such as a polyimide for flexibility, or a combination of metal at the proximal end 210 and transitioning to the polymeric material as it extends toward the distal end 212. In some examples the inflation tube 104 may be used to advance the balloon assist device 100 along the catheter 240 in the distal direction and to retract it in the proximal direction. In other embodiments a separate pusher (not shown) may be attached to the inner body 204 to advance the balloon assist device 100 along the catheter 240 in the distal direction and to retract it in the proximal direction, allowing the inflation tube to be more flexible.

After sealing the sheath 214 to the inner body 204, the flat balloon assembly 200 can be formed into an appropriate shape for mounting to the catheter 240. In certain examples, the balloon assist device 100 can be manufactured/shipped in the flat orientation and bent around the catheter by a clinician. The final shape of the inner body 204 partially encloses the catheter 240 securely enough to track along catheter body inside the patient's vasculature during a procedure. In the embodiment shown the inner body 204 has a cylindrical shape, but other cross-sections may be used as needed.

Figure 6:
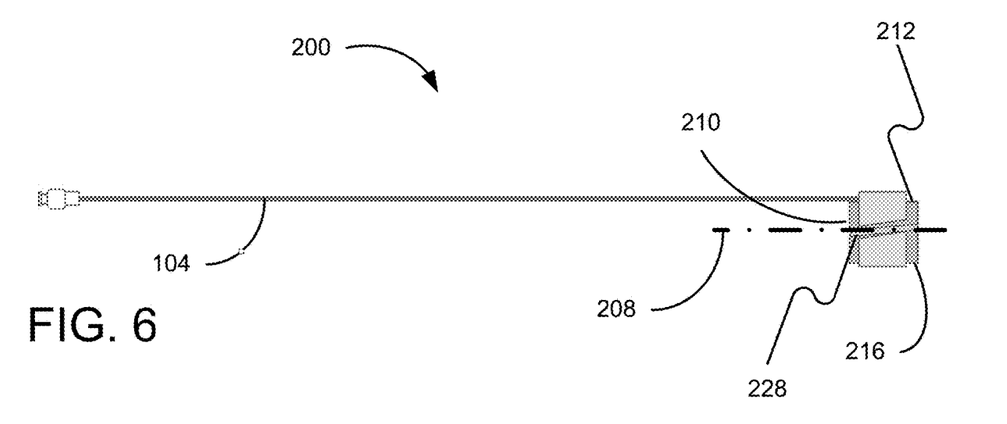
FIG. 6 is a diagram of an alternate embodiment of the balloon assist device where the inner body has a helical slit, in accordance with the present disclosure.
Figure 7:
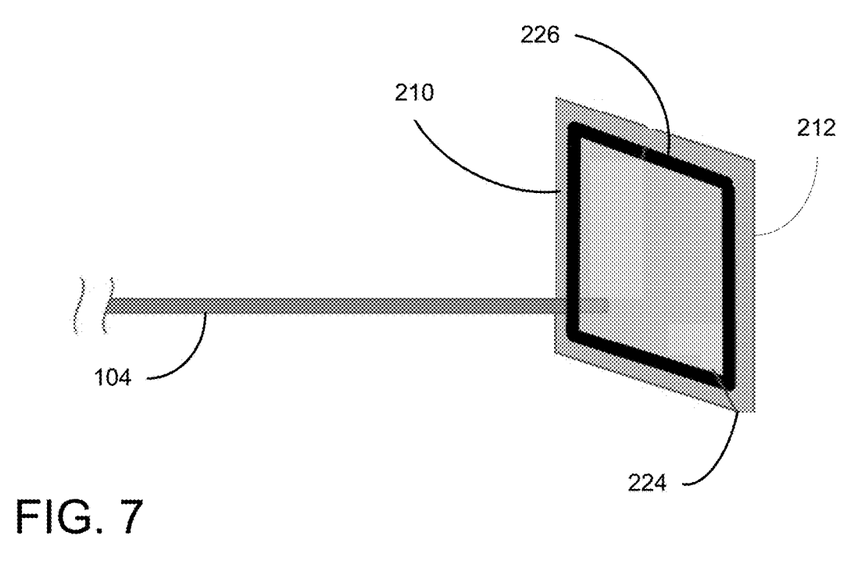
FIG. 7 is a diagram of an alternate embodiment of the balloon assembly of the balloon assist device illustrating the balloon and inner body in a flattened state, where the inner body has a helical slit, in accordance with the present disclosure.

In the embodiment shown in FIG. 5, the slit 206 in the inner body 204 is straight. That is, the slit 206 is parallel to the axis 208 and to the catheter 240. An alternative embodiment with a helical slit 228 is shown in FIG. 6. In this embodiment, the helical slit 214 coils around the axis 208 and the catheter 240 at least a quarter turn. A pre-formed flat version of this embodiment is shown in FIG. 7 as a non-limiting example to form the helical slit 228. Instead of rectangles, the inner body 224 and sheath 226 are cut into trapezoids (not illustrated). When these are formed into a cylinder they result in the helical slit 228.

Figure 8:
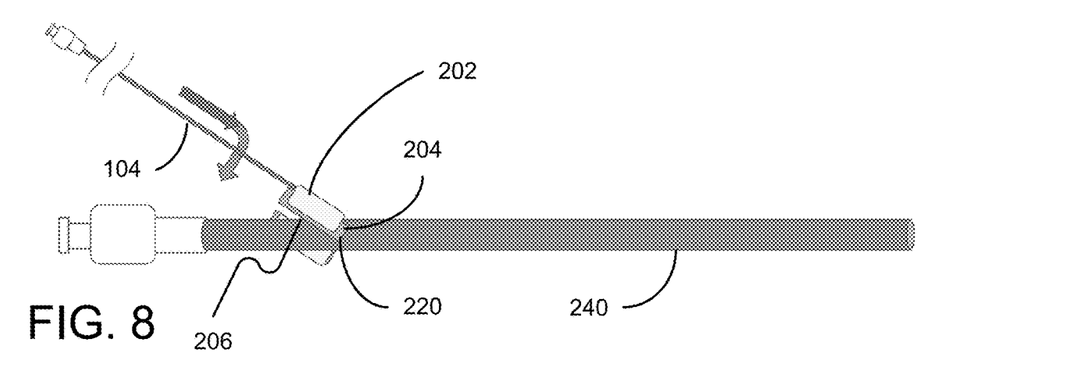
FIG. 8 is a diagram of the balloon assist device being mounted to the proximal end of the catheter body, in accordance with the present disclosure.
Figure 9:
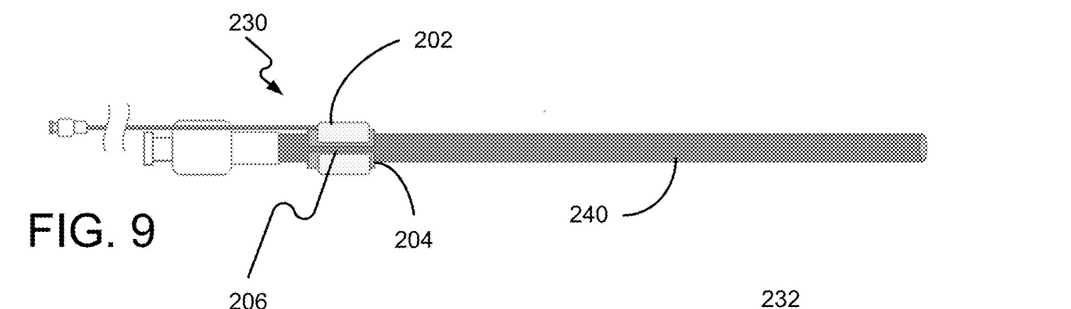
FIG. 9 is a diagram of the balloon assist device mounted on the proximal end of the catheter body, in accordance with the present disclosure.
Figure 10:
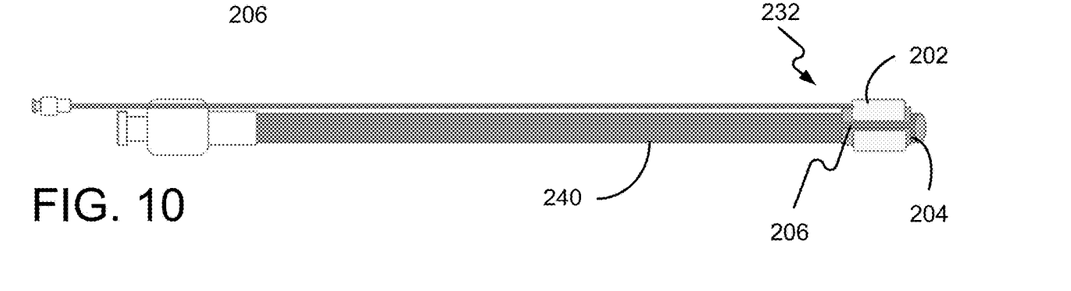
FIG. 10 is a diagram of the balloon assist device mounted on the catheter body and positioned at the distal end of the catheter, in accordance with the present disclosure.
Figure 11:
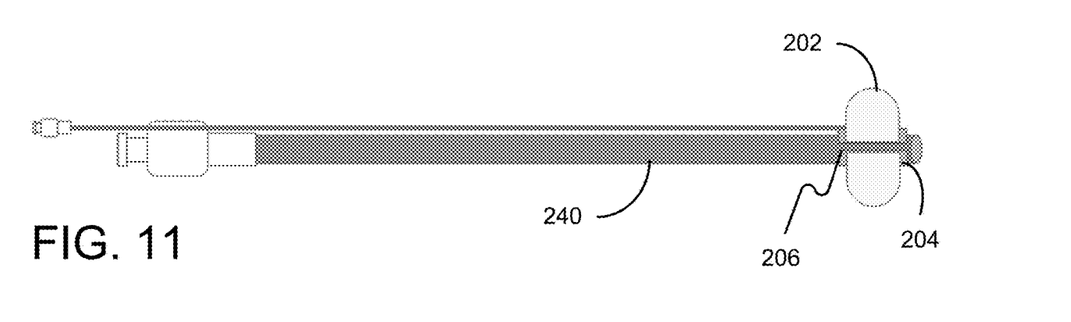
FIG. 11 is a diagram of the balloon assist device balloon inflated at the distal end of the catheter in accordance with the present disclosure.

FIGS. 8-11 show the basic operation of the balloon assist device 100. In FIG. 9 the balloon assist device 100 is mounted on the catheter 240. As explained above, the slit 206 is spread wide enough to accept the catheter 240. To ease the process, a corner 220 of the slit 206 may be initially spread to accept the catheter 240 and the process completed by twisting the balloon assist device 100 the rest of the way onto the catheter 240, as shown in FIG. 8. FIG. 9 shows the balloon assist device 100 fully mounted on the catheter 240 in a proximal position 230. The balloon assist device 100 is then slid along the catheter 240 using the inflation tube 104 or a separate pusher (not illustrated). FIG. 10 shows the balloon assist device 100 mounted on the catheter 240 in the distal position 232 after sliding along the catheter 240. The balloon 202 is then inflated using the inflation tube 104, as shown in FIG. 11.

Figure 12:
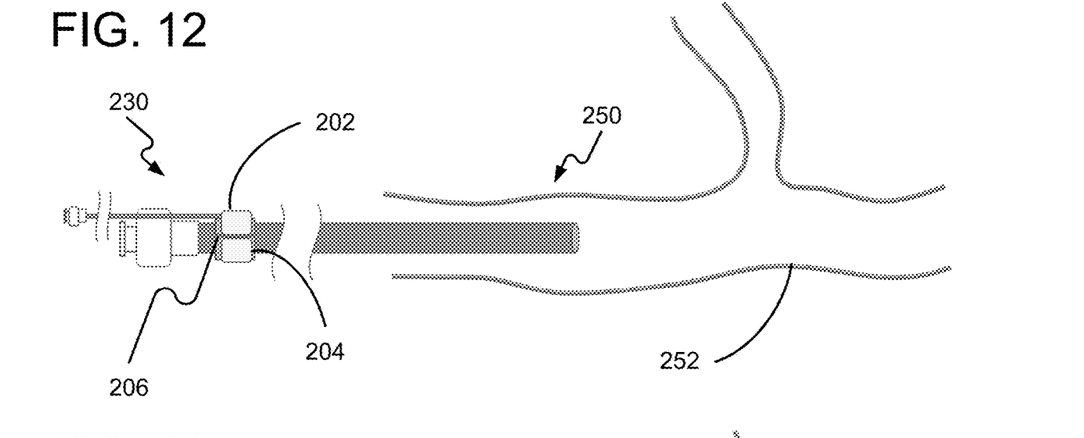
FIG. 12 is a diagram of a catheter positioned in a patient's vasculature with the balloon assist device mounted to the proximal end of the catheter body, in accordance with the present disclosure.
Figure 13:
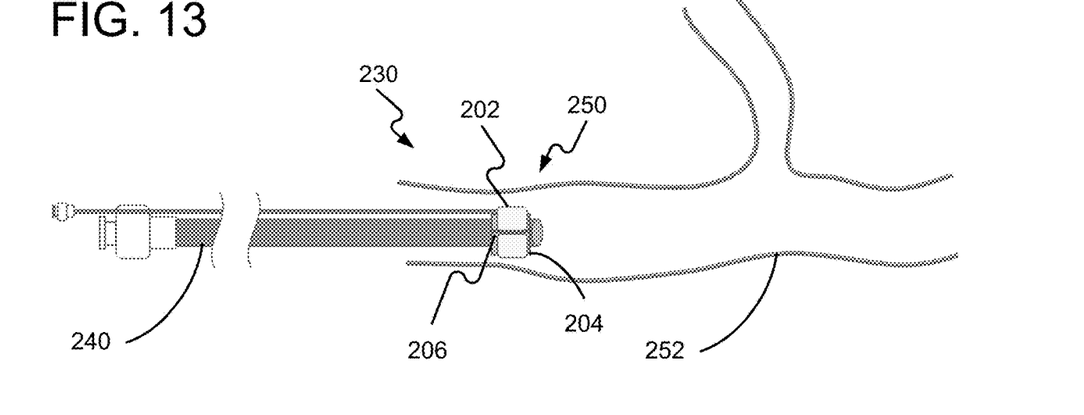
FIG. 13 is a diagram of a catheter positioned in a patient's vasculature with the balloon assist device positioned on the distal end of the catheter body at the treatment site, in accordance with the present disclosure.
Figure 14:
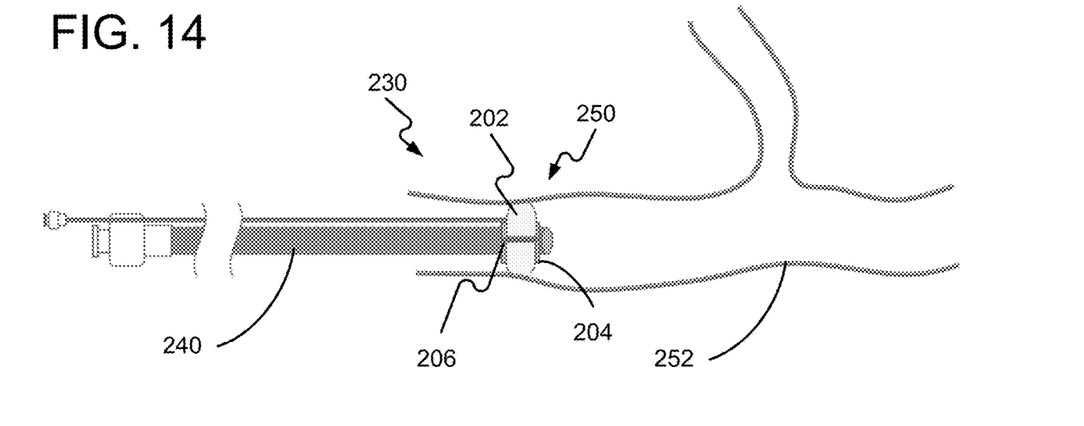
FIG. 14 is a diagram of a catheter positioned in a patient's vasculature with the balloon inflated at the treatment site, occluding a blood vessel, in accordance with the present disclosure.

FIGS. 12-14 show the basic operation of the balloon assist device 100 during a medical procedure. FIG. 12 shows the balloon assist device 100 fully mounted in the proximal position 230 on a catheter 240 which a clinician has already positioned at a treatment site 250 within a patient's vasculature 252. The balloon assist device 100 is then slid along the catheter 240 using the inflation tube 104 or a separate pusher (not illustrated) to treatment site 250. FIG. 10 shows the balloon assist device 100 mounted on the catheter 240 in the distal position 232 at the treatment site 250. The balloon 202 is then inflated using the inflation tube 104 to occlude part of the patient's vasculature 252, as shown in FIG. 11.

Figure 15:
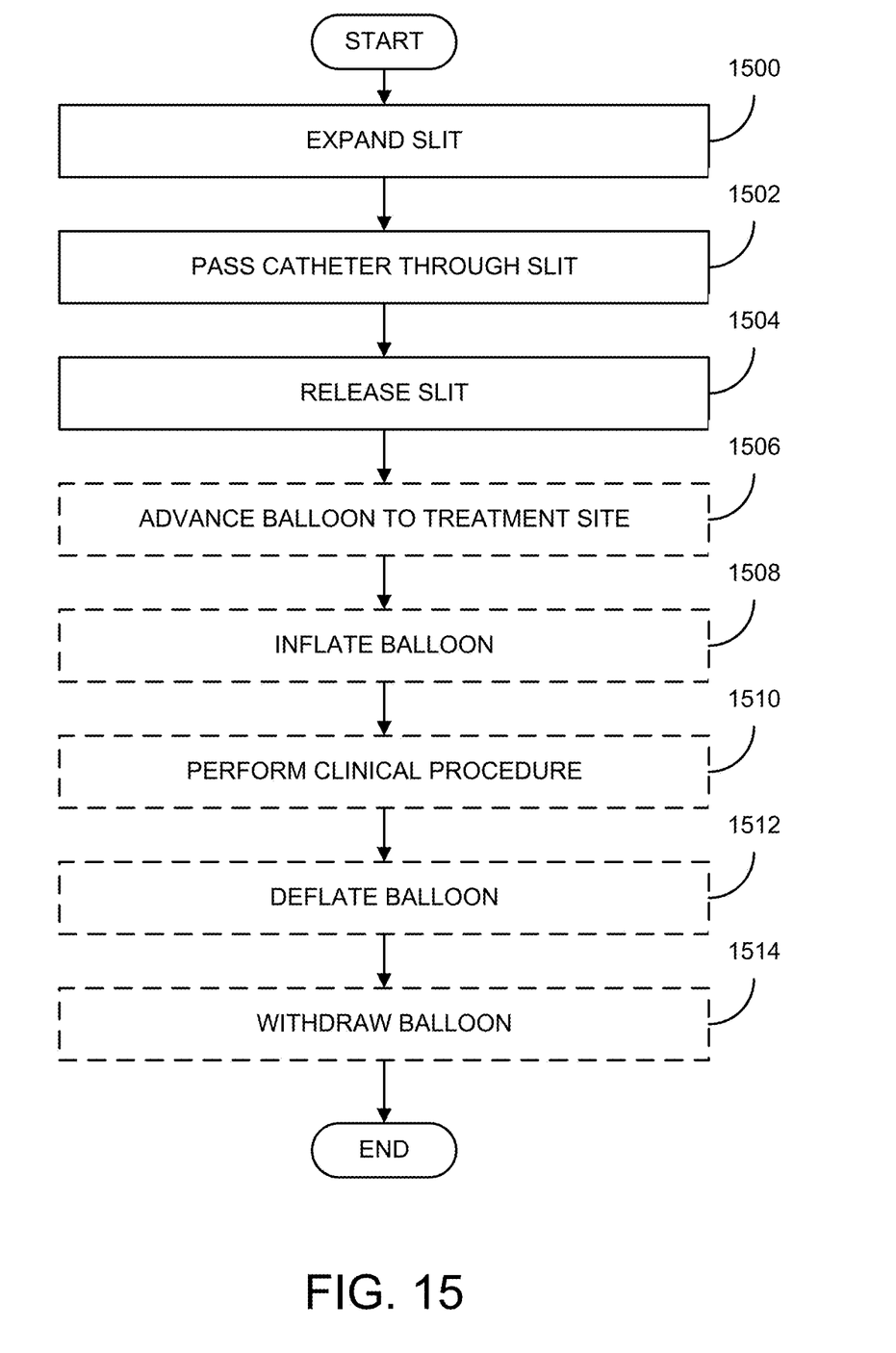
FIG. 15 is a flow chart illustrating one embodiment of a method for using the balloon assist device, in accordance with the present disclosure.

FIG. 15 is flow chart showing the steps for using the balloon assist device 100. At 1500 the slit 206 is expanded. At 1502 the catheter 240 is inserted through the expanded slit 206. At 1504 the expanded slit 206 is released to contract around the catheter 240, securely and slidably mounting the balloon assist device 100 to the catheter 240. The remaining steps are optional based on the clinical procedure. At 1506 a pusher is used to slide the balloon assist device 100 along the catheter 240 to a treatment site 250 in a patient's vasculature 252. In some embodiments the pusher may be the inflation tube 104. At 1508 the balloon assist device 100 is inflated at the treatment site 250 using the inflation tube 104. Alternately, at 1510 a procedure is performed while the inflated balloon assist device 100 occludes a blood vessel at the treatment site 250. At 1512 the balloon assist device 100 is deflated. At 1514 the deflated balloon assist device 100 is withdrawn.

To facilitate an understanding of the principals and features of the disclosed technology, illustrative embodiments are explained below. The components described hereinafter as making up various elements of the disclosed technology are intended to be illustrative and not restrictive. Many suitable components that would perform the same or similar functions as components described herein are intended to be embraced within the scope of the disclosed devices and methods. Such other components not described herein may include, but are not limited to, for example, components developed after development of the disclosed technology.

It must also be noted that, as used in the specification and the appended claims, the singular forms "a," "an" and "the" include plural referents unless the context clearly dictates otherwise.

By "comprising" or "containing" or "including" is meant that at least the named component or method step is present in the article or method, but does not exclude the presence of other components or method steps, even if the other such components or method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

Certain embodiments of this technology are described above with reference to flow diagrams. Some blocks of the block diagrams and flow diagrams may not necessarily need to be performed in the order presented, or may not necessarily need to be performed at all, according to some embodiments of the disclosure.

While certain embodiments of this disclosure have been described in connection with what is presently considered to be the most practical and various embodiments, it is to be understood that this disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the technology and also to enable any person skilled in the art to practice certain embodiments of this technology, including making and using any apparatuses or systems and performing any incorporated methods. The patentable scope of certain embodiments of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method, comprising:
    joining a balloon to a resilient inner body of a balloon assist device, the balloon comprising an axial length shorter than an axial length of the inner body;
    expanding a slit in the resilient inner body of the balloon assist device;
    inserting a catheter through the slit; and
    releasing the slit to contract the balloon assist device around the catheter.

2. The method of claim 1 further comprising using a pusher to slide the balloon assist device along the catheter to a treatment site in a patient's vasculature.

3. The method of claim 2 further comprising using an inflation tube to inflate the balloon assist device at the treatment site.

4. The method of claim 3 further comprising performing a surgical procedure while the inflated balloon assist device occludes a blood vessel at the treatment site.

5. The method of claim 4 further comprising deflating the balloon assist device; and
    withdrawing the deflated balloon assist device.

6. The method of claim 1 the inner body comprising a split cylinder comprising a cross-section divided by the slit radially offset from the axis of the inner body and in sealed communication with a balloon which partially encloses the axis.

7. The method of claim 1 further comprising radially offsetting an inflation tube from the axis of the inner body and in sealed communication with the balloon.

8. The method of claim 1 further comprising
    attaching the inner body and the balloon onto an inner surface of the catheter; and advancing both the inner body and the balloon along the outer surface of the catheter from a proximal position of the catheter to a distal position of the catheter.

9. The method of claim 1 the balloon comprises a sheath of flexible material separate from and bonded to the inner body and a volume between the sheath and the inner body which comprises an interior of the balloon.

10. The method of claim 1 wherein the slit comprises a straight slit.

11. The method of claim 1 wherein the slit comprises a helical slit.

\* \* \* \* \*